United States Patent
Lee et al.

(10) Patent No.: US 8,680,309 B2
(45) Date of Patent: Mar. 25, 2014

(54) METAL ORGANIC PRECURSOR, A METHOD OF PREPARING THE SAME, AND A METHOD OF FORMING A CONDUCTIVE METAL FILM OR PATTERN

(75) Inventors: Jae Ho Lee, Yongin-si (KR); Young Hun Byun, Suwon-si (KR)

(73) Assignee: Samsung Electronics Co., Ltd. (KR)

( * ) Notice: Subject to any disclaimer, the term of this patent is extended or adjusted under 35 U.S.C. 154(b) by 474 days.

(21) Appl. No.: 12/953,903

(22) Filed: Nov. 24, 2010

(65) Prior Publication Data

US 2011/0135823 A1  Jun. 9, 2011

(30) Foreign Application Priority Data

Dec. 7, 2009  (KR) ........................ 10-2009-0120634

(51) Int. Cl.
*C07F 1/00* (2006.01)
*C07F 15/00* (2006.01)
*B05D 5/00* (2006.01)
*H01B 1/00* (2006.01)

(52) U.S. Cl.
USPC ........ 556/116; 556/137; 427/256; 427/383.1; 427/383.3; 427/383.5; 252/519.21

(58) Field of Classification Search
USPC ............ 556/116, 137; 427/256, 383.1, 383.3, 427/383.5; 252/519.21
See application file for complete search history.

(56) References Cited

U.S. PATENT DOCUMENTS 7,084,288 B2 *  8/2006  Son et al. ...................... 556/137

FOREIGN PATENT DOCUMENTS

| KR | 1020040071193 A | 8/2004 |
|---|---|---|
| KR | 1020040078467 A | 9/2004 |
| KR | 10-0893564 A | 4/2009 |

OTHER PUBLICATIONS

Gerasimenko et al., Acta Crystallographica, Section E: Structure Reports Online, vol. 61, No. o, pp. m1816-m1817 (2005).*
Romanenko et al., Journal of Structural Chemistry, vol. 40, No. 1, pp. 159-162 (1999).*

* cited by examiner

*Primary Examiner* — Porforio Nazario Gonzalez
(74) *Attorney, Agent, or Firm* — Cantor Colburn LLP

(57) ABSTRACT

A metal organic precursor, including a metal-chelate complex including a chelate including a Groups 3 to 12 metal ion, a chelating ligand, and an anion bound to the chelate, wherein the chelating ligand forms a reducing compound and a volatile material at a temperature of about 160° C. or lower, the anion forms a reducing compound and a volatile material at a temperature of about 180° C. or lower, and the metal-chelate complex is represented by Formula I:

$$[L1\text{-}Me]_p^{n+}[A]_q^{m-} \qquad (I)$$

wherein Me is the Groups 3 to 12 metal ion, L1 is the chelating ligand, A is the anion, n, m, p, and q are independently integers of 1 or more, n is the sum of a charge quantity of L1 and a charge quantity of Me, m is a charge quantity of A, and (n×p)=(m×q).

16 Claims, 3 Drawing Sheets

METAL ORGANIC PRECURSOR, A METHOD OF PREPARING THE SAME, AND A METHOD OF FORMING A CONDUCTIVE METAL FILM OR PATTERN

CROSS-REFERENCE TO RELATED APPLICATION

This application claims priority to Korean Patent Application No. 10-2009-00120634, filed on Dec. 7, 2009, and all the benefits accruing therefrom under 35 U.S.C. §119, the content of which in its entirety is herein incorporated by reference.

BACKGROUND

1. Field

This disclosure relates to a metal organic precursor, a method of preparing the same, and a method of forming a conductive metal film or pattern.

2. Description of the Related Art

Metal interconnections are a desirable method for electrically connecting semiconductor devices and discrete devices, such as transistors, to one another. Currently, in accord with a trend of more highly integrated semiconductor devices, in an electronic device, such as an integrated circuit or a liquid crystal display device, the characteristic dimension (e.g. line width) of a metal interconnection pattern, which may be formed on a substrate, has become smaller to accommodate increased integration and miniaturization of the devices.

To form a finer metal interconnection pattern (i.e., having a smaller characteristic dimension), photolithography using a photoresist is employed commercially. In a commercially practiced photolithographic method, after a metal material layer, which is a base of an interconnection, is formed on a substrate by chemical vapor deposition ("CVD"), plasma deposition, or electroplating, a photoresist is applied onto the metal material layer, and the photoresist is exposed and developed using a photomask, thereby forming a metal layer having the patterned photoresist layer. Afterwards, the metal layer is etched by reactive ion etching, to provide a metal interconnection having a pattern on the substrate.

As an alternative to photolithography, soft lithography and inkjet printing, which are capable of forming a fine pattern on a substrate more-simply, have attracted attention. These simple and convenient methods can form a fine metal pattern at a lower cost.

However, there remains a need for a material which can be disposed on a substrate, by a method such as printing, and which can provide a metal film when treated at a low temperature.

SUMMARY

Exemplary embodiments provide a metal organic precursor which can be metalized at low temperature.

Exemplary embodiments also provide a technology capable of forming a metal film or pattern having high conductivity, e.g., a conductivity corresponding to a pure metal, by a simple process which may be performed at low temperature.

According to an aspect, a metal organic precursor includes a metal-chelate complex including a chelate including a Groups 3 to 12 metal ion and a chelating ligand, and an anion bound to the chelate, wherein the chelating ligand produces a reducing compound and a volatile material at a temperature of about 160° C. or lower, the anion forms a reducing compound and a volatile material at a temperature of about 180° C. or lower, and the metal-chelate complex is represented by Formula I.

$$[L1\text{-}Me]_p^{n+}[A]_q^{m-} \quad (I)$$

In Formula I, Me is a Groups 3 to 12 metal ion, L1 is the chelating ligand, A is the anion, n, m, p, and q are independently integers of 1 or more, n the sum of a charge quantity of Me and a charge quantity of L1, and m is a charge quantity of A, and (n×p)=(m×q).

The Groups 3 to 12 metal ion (Me) may be Cu, Ag, Pt, Pd, Au, Ni, or a combination including at least one of the foregoing.

The chelating ligand (L1) may be a hydrazine derivative having an N—N bond and that forms $NH_2$—$NH_2$ an alcohol, an alkene, $H_2$, $H_2O$, $CO_2$, or a combination including at least one of the foregoing.

The chelating ligand (L1) may be hydrazine alkyl ester represented by Formula II:

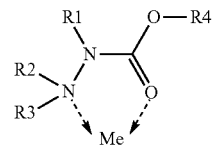

(II)

wherein R1, R2, R3, and R4 are each independently hydrogen, a $C_1$-$C_{10}$ alkyl, $C_6$-$C_{12}$ aryl, $C_1$-$C_{10}$ alkylalkoxy, or $C_6$-$C_{12}$ arylalkoxy, each of which may be unsubstituted or substituted with a halogen, amine, —OH, —SH, cyano, or sulfonyl.

The anion (A) may be formate, oxalate, or a combination including at least one of the foregoing.

The anion (A) may be a compound containing an aldehyde (—CHO) group that forms OCHO, an alcohol, an alkene, $H_2$, $H_2O$, $CO_2$, or a combination including at least one of the foregoing.

The compound (A) may be represented by Formula III.

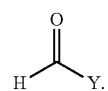

(III)

In Formula III, Y is oxygen, $C_1$-$C_{10}$ alkyl carboxylate, $C_1$-$C_{10}$ alkyl sulfonate, or a combination including at least one of the foregoing.

In one example, the complex represented by Formula I may be a metal-chelate complex represented by Formula IV,

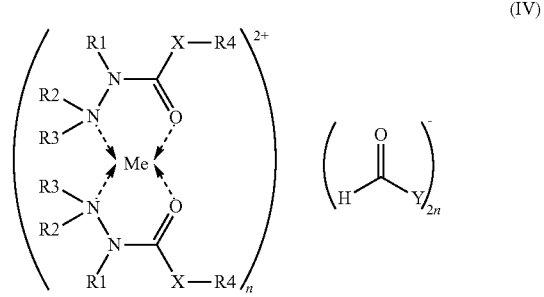

(IV)

wherein, n is an integer of 1 or more; Me is a Groups 3 to 12 metal ion; X is hydrogen, nitrogen, or oxygen, and R1, R2, R3, and, when X is nitrogen or oxygen, R4, is hydrogen, a $C_1$-$C_{10}$ alkyl, $C_6$-$C_{12}$ aryl, $C_1$-$C_{10}$ alkylalkoxy, or $C_6$-$C_{12}$ arylalkoxy, each of which may be unsubstituted or substituted with halogen, amine, —OH, —SH, cyano, sulfonyl, or a combination including at least one of the foregoing, provided that when X is nitrogen the valence of the nitrogen is satisfied by two independently selected R4 groups; and Y is oxygen, $C_1$-$C_{10}$ alkyl carboxylate, $C_1$-$C_{10}$ alkyl sulfonate, or a combination including at least one of the foregoing.

The metal organic precursor may further include a neutral ligand (L2).

For example, the neutral ligand may be one or more of (i) alkene, (ii) alkyl, (iii) silicon, or (iv) an organic ligand including one or more of sulfur (S), oxygen (O), phosphorus (P), nitrogen (N), or a combination including at least one of the foregoing.

In some embodiments, the metal organic precursor may further include a solvent or vehicle such as water; an amine-based solvent; an ester-based solvent; a ketone-based solvent; an aliphatic or aromatic hydrocarbon-based solvent; an alcohol-based solvent; a polyol solvent; an amide-based solvent; a sulfoxide-based solvent; an acetate-based solvent; an inorganic solvent; or a combination including at least one of the foregoing.

The metal organic precursor may have a metallization temperature of about 150° C. or lower, 140° C. or lower, 130° C. or lower, 120° C. or lower, or 110° C. or lower.

According to another aspect, a method of forming a conductive metal organic precursor is provided. In an example, the method may include preparing a metal organic precursor, the metal organic precursor including a metal-chelate complex including a chelate including a Groups 3 to 12 metal ion and a chelating ligand, and an anion bound to the chelate, wherein the chelating ligand forms a reducing compound and a volatile material at a temperature about 160° C., the anion forms a reducing compound and a volatile material at a temperature of about 180° C., and the metal-chelate complex is represented by Formula I:

wherein Me is the Groups 3 to 12 metal ion, L1 is the chelating ligand, A is the anion, n, m, p, and q are independently integers of 1 or more, n is the sum of a charge quantity of L1 and a charge quantity of Me, m is a charge quantity of A, and (n×p)=(m×q); coating the metal organic precursor on a substrate; and heat treating the metal organic precursor to form a conductive metal film.

The processes may be performed at a low temperature of 25° C. or lower. The chelating ligand (L1), a chelating agent, may be hydrazine alkyl ester represented by Formula II. The anion (A) may be a compound represented by Formula III.

According to still another aspect, a method of forming a conductive metal film or pattern using the metal organic precursor described above or a composition including the same is provided.

For example, the method may include preparing the metal organic precursor or a composition including the same; coating the metal organic precursor or composition on a substrate; and performing heat treatment.

The substrate may be a semiconductor; an inorganic material such as a metal, a silicon wafer, a glass, or a ceramic; a polymer such as polyimide ("PI"), polyethylene naphthalate ("PEN"), polyethylene terephthalate ("PET"), polyestersulfone ('PES"), polypropylene ("PP"), oriented polypropylene ("oPP"), cycloolefin-based polymer, or polycarbonate ("PC"); a rubber sheet; a cellulose-based material such as fabric, wood, paper, or cellulose; or a combination including at least one of the foregoing.

To coat the precursor or composition on the substrate, a method such as spin coating, roll coating, deep coating, spray coating, dip coating, flow coating, doctor blade, dispensing, inkjet printing, screen printing, gravure printing, offset printing, pad printing, flexography printing, stencil printing, imprinting, xerography, or lithography may be used.

The heat treating may be performed at about 180° C. or lower.

Also disclosed is a composition including the metal organic precursor.

BRIEF DESCRIPTION OF THE DRAWINGS

The above and other aspects, advantages, and features of this disclosure will become more apparent by describing in further detail representative embodiments with reference to the accompanying drawings, in which.

DETAILED DESCRIPTION

Figure 1:
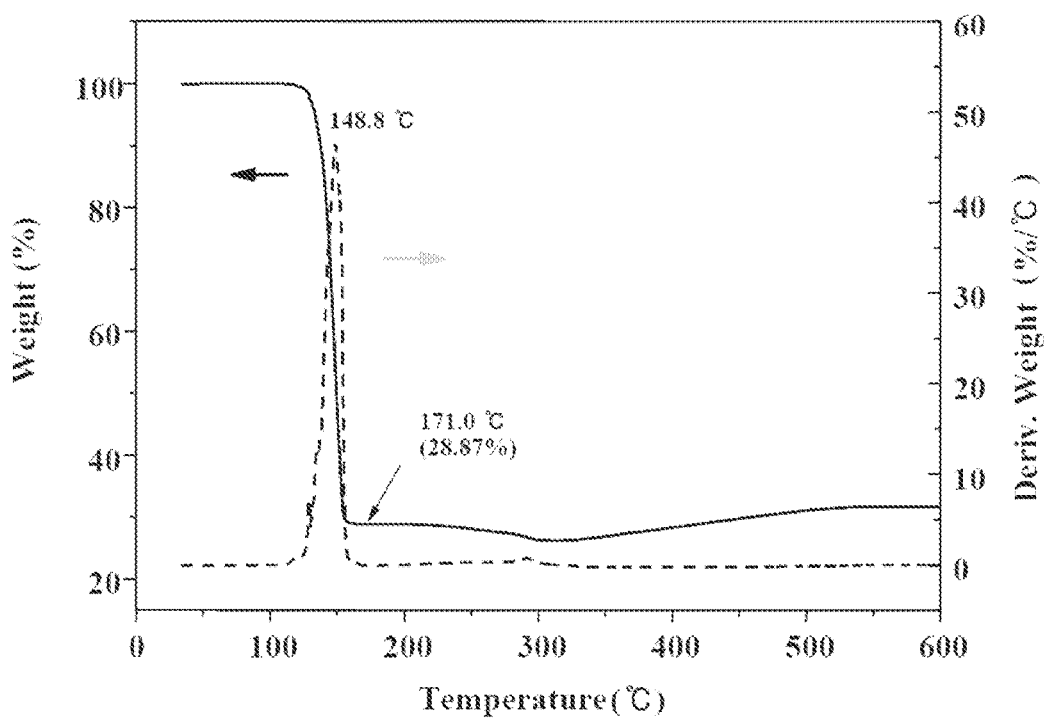
FIG. 1 is a graph of weight (percent, %) and derivative of weight (percent per degrees centigrade, %/° C.) versus temperature (degrees centigrade, ° C.) which shows the TGA results for a metal organic precursor prepared according to Example 1.

Various representative embodiments will now be further disclosed with reference to the accompanying drawings in which some exemplary embodiments are shown. This invention may, however, be embodied in many different forms, and should not be construed as limited to the embodiments set forth herein. Rather, these embodiments are provided so that this disclosure will be thorough and complete, and will fully convey the scope of the invention to those skilled in the art. In the drawings, the thicknesses of layers and regions may be exaggerated for clarity. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer, or section from another element, component, region, layer or section. Thus, a first element, component, region, layer, or section discussed below could be termed a second element, component, region, layer, or section without departing from the teachings of the present invention.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups including at least one of the foregoing.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, unless otherwise provided, the term "substituted" refers to a compound or radical substituted with at least one (e.g., 1, 2, 3, 4, 5, 6 or more) substituents independently selected from a halogen (e.g., F, Cl, Br, I), amine, hydroxyl, thiol, cyano, sulfonyl, or a combination including at least one of the foregoing, instead of hydrogen, provided that the substituted atom's normal valence is not exceeded.

As used herein, unless otherwise provided, term "alkyl" refers to a linear, branched, or cyclic saturated aliphatic hydrocarbon. Alkyl groups include, for example, groups having from 1 to 50 carbon atoms (C1-C50 alkyl). For example, the alkyls include linear and branched radicals such as methyl, ethyl, n-propyl, isopropyl, n-butyl, sec-butyl, isobutyl, ten-butyl, 2-ethyl hexyl, pentyl, hexyl, heptyl, octyl, nonyl, decyl, undecyl, and dodecyl radicals, and cyclic alkyl radicals such as cyclopropyl, cyclobutyl, cyclopentyl, cyclohexyl, cycloheptyl, and cyclooctyl.

As used herein, unless otherwise provided, the term "aryl" means a cyclic moiety in which all ring members are carbon and at least one ring is aromatic. More than one ring may be present, and any additional rings may be independently aromatic, saturated or partially unsaturated, and may be fused, pendant, spirocyclic or a combination including at least one of the foregoing. For example, an aryl group may include a six to twelve-membered aromatic carbon ring. Representative aryl groups include, for example, phenyl, naphthyl, and alkyl-substituted aryl.

As used herein, unless otherwise provided, the term "halogen" includes fluorine, chlorine, bromine, and iodine.

As used herein, unless otherwise provided, the term "Group" refers to a group of the periodic table of the elements according to the International Union of Pure and Applied Chemistry ("IUPAC") 1-18 group classification system.

As used herein, particle size refers to an average longest particle dimension.

1. Metal Organic Precursor

According to an exemplary embodiment, a metal organic precursor comprises a metal-chelate complex represented by Formula I and may be used to form a conductive film or pattern.

$$[L1\text{-}Me]_p^{n+}[A]_q^{m-} \qquad (I)$$

In Formula I, Me is a Groups 3 to 12 metal ion, which may be, but is not limited to, Cu, Ag, Pt, Pd, Au, Ni, or a combination comprising at least one of the foregoing.

L1 is a chelating ligand, which, without being bound by theory, is degraded to form a reducing compound and a volatile compound at a temperature of about 160° C. or lower, specifically about 150° C.° or lower, more specifically about 130° C. or lower, more specifically about 120° C. or lower, even more specifically about 100° C. or lower.

A is an anion, which, without being bound by theory, is degraded to form a reducing compound and a volatile material at a temperature of about 180° or lower, specifically about 160° C. or lower, more specifically about 150° C. or lower, more specifically about 130° C. or lower, more specifically about 120° C. or lower, even more specifically about 100° C. or lower.

In a representative embodiment, n, m, p, and q are independently integers of 1 or more, respectively, wherein n is a charge quantity of Me or the sum of a charge quantity of L1 and a charge quantity of Me, m is a charge quantity of A, and Formula I satisfies the equation (n×p)=(m×q).

From the metal-chelate complex described herein, the chelating ligand (L1) and/or the anion (A) may not generate an undesirable non-volatile residue, which may undesirably be included in a metal film during or resulting from thermal degradation or reduction of the metal organic precursor at low temperature. The volatile degradation products of the metal-chelate complex, specifically the volatile degradation products of the chelating ligand and/or the anion of the metal organic precursor, may be completely removed. Thus, a degradation temperature to provide a metal from the metal organic precursor can be decreased, and a metal yield can be increased.

The chelating ligand (L1) forms a chelate by a coordinate covalent bond with the Groups 3 to 12 metal ion (Me). The term "chelate" refers to a complex ion or complex compound, in which a ligand including at least two elements having a non-covalent electron pair, is bound to the Groups 3 to 12 metal ion (Me), thereby being configured in a ring structure.

The metal-chelate complex may comprise one ligand, or may comprise a plurality of chelating ligands (L1), and the number of chelating ligands may be the same or less than the number of coordinate covalent bonds (n) of the Groups 3 to 12 metal ion (Me). In an embodiment, metal chelate complex may comprise 1 to about 18 chelating ligands, specifically about 2 to about 16 chelating ligands, more specifically about 3 to about 14 chelating ligands. A representative number of coordinate covalent bonds according to the type of the Groups 3 to 12 metal ion (Me) is shown in Table 1

TABLE 1

| Number of Coordinate covalent bonds | Groups 3 to 12 metal ion (Me) |
|---|---|
| 2 | $Ag^+$, $Cu^+$ |
| 4 | $Cu^{2+}$, $Zn^{2+}$, $Ni^{2+}$, $Pb^{2+}$ |
| 6 | $Co^{3+}$, $Fe^{3+}$, $Cr^{3+}$, $Sn^{2+}$, $Ag^+$, $Cu^{2+}$ |

The metal-chelate complex exhibits a good stability as compared to a complex including one non-covalent electron pair. Further, the chelating ligand (L1) is degraded to form a reducing compound, for example, hydrazine.

In an example, the chelating ligand (L1) is a hydrazine derivative including an N—N bond, and may be a compound that forms a reducing compound such as hydrazine ($NH_2$—$NH_2$), an alcohol, an alkene, $H_2$, $H_2O$, $CO_2$, or a combination comprising at least one of the foregoing, as a degradation product.

Hydrazine ($NH_2$—$NH_2$) may be oxidized to form nitrogen gas, ammonia gas, hydrogen gas, or a combination comprising at least one of the foregoing, as shown in the following Reaction Formulae i, ii, and iii, thereby reducing a metal ion into metal.

  [Reaction Formula i]

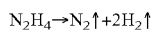  [Reaction Formula ii]

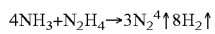  [Reaction Formula iii]

In a representative example, the chelating ligand (L1) may be a hydrazine alkyl ester represented by Formula II:

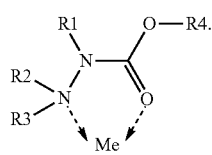

(II)

In Formula II, R1, R2, R3 and R4 are each independently hydrogen, or a $C_1$-$C_{10}$ alkyl, $C_6$-$C_{12}$ aryl, $C_1$-$C_{10}$ alkylalkoxy, or $C_6$-$C_{12}$ arylalkoxy, each of which may be substituted or unsubstituted with a halogen, amine, —OH, —SH, cyano, sulfonyl, or a combination comprising at least one of the foregoing.

Examples of such a hydrazine alkyl ester may include, but are not limited to, hydrazine methyl ester, hydrazine ethyl ester, and hydrazine t-butyl ester.

The chelating ligand (L1) forms a chelate by a coordinate covalent bond between the Groups 3 to 12 metal ion (Me) and a non-covalent electron pair present in the nitrogen or the oxygen thereof. In addition, as shown in Reaction Formula I, the chelating ligand (L1) is degraded at a temperature of about 160° C. or lower, specifically about 150° C. or lower, more specifically about 130° C. or lower, more specifically about 120° C. or lower, even more specifically about 100° C. or lower, to generate a reducing material such as hydrazine and a volatile material such as alcohol and carbon dioxide. Such volatile materials are easily removed, and thus do not generate impurities.

[Reaction Formula 1]

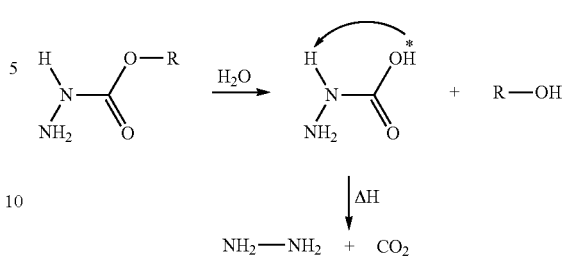

The anion (A) serves to electrically neutralize a metal-ligand chelate, and may or may not be coordinated to the Groups 3 to 12 metal ion (Me). The anion (A) may be a material which degrades to form a reducing compound and a volatile material at about 180° C. or lower. For example, the anion (A) may be, but is not limited to, formate, oxalate, or a combination comprising at least one of the foregoing. Thus the anion (A) has a negative charge to balance the positive charge of the metal ion, and thus A is not a neutral species, such as an ester or sulfonyl ester, for example.

In an example, the anion (A) is a compound containing an aldehyde group (—CHO), represented by Formula III.

(III)

In Formula III, Y is oxygen, $C_1$-$C_{10}$ alkyl carboxylate, $C_1$-$C_{10}$ alkyl sulfonate, or a combination comprising at least one of the foregoing.

The compound may produce a reducing compound such as formate (OCHO) and a volatile material such as an alcohol, alkene, $H_2$, $H_2O$, $CO_2$, or a combination comprising at least one of the foregoing, as a degradation product.

Formate, one of the degradation products, has excellent solubility in water, a specific gravity of 12.203 (at 20° C.), a boiling point of 100.8° C., a melting point of 8.4° C., and a vapor pressure of 33.1 mmHg (at 20° C.). When formate is heated to about 160° C. or higher in an air or vapor atmosphere, it is dissociated into carbon dioxide and hydrogen. Moreover, because formate has strong reducing power, it aids reduction of the Groups 3 to 12 metal ion (Me) to a metal. In other words, formate may be oxidized into carboxylic acid and thus can serve as a reducing agent. The product obtained by reduction, carbon dioxide, is easily removed, and thus no residual impurities remain on a copper film, which is previously formed.

For example, copper formate is reduced to produce a volatile material, such as $CO_2$, $CO$, or $H_2O$, as a degradation product, each of which is easily removed by thermal degradation as shown in Reaction Formulae iv and v. More specifically, the degradation of copper formate produces only gaseous by-products, which protect copper formed in situ from oxidation.

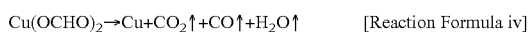  [Reaction Formula iv]

  [Reaction Formula v]

In an example, the complex represented by Formula I may be a metal-chelate complex, which is represented by Formula IV.

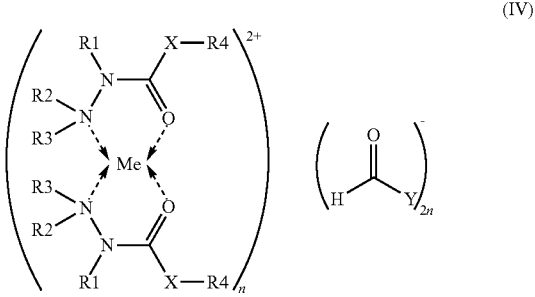

(IV)

In Formula IV, n is an integer of 1 or more, and Me is a Groups 3 to 12 metal ion. For example, Me may be a bivalent metal ion such as $Cu^{2+}$, X may be hydrogen, nitrogen or oxygen, and R1, R2, R3, and, when X is nitrogen or oxygen R4, are each independently selected from hydrogen, a $C_1$-$C_{10}$ alkyl, $C_6$-$C_{12}$ aryl, $C_1$-$C_{10}$ alkylalkoxy, or $C_6$-$C_{12}$ arylalkoxy, each of which may be unsubstituted or substituted with a halogen, amine, —OH, —SH, cyano, sulfonyl, or a combination comprising at least one of the foregoing, provided that when X is nitrogen the valence of the nitrogen is satisfied by two independently selected R4 groups; and Y is oxygen, $C_1$-$C_{10}$ alkyl carboxylate, $C_1$-$C_{10}$ alkyl sulfonate, or a combination including at least one of the foregoing.

In the metal organic precursor, a reducing agent, hydrazine, is generated from the chelating ligand (L1), hydrazine alkyl ester, and another reducing agent, such as aldehyde, is generated from an anion (A), an aldehyde-based compound. Accordingly, without adding separate reducing agent, reduction of the Groups 3 to 12 metal ion to a metal can be performed with a high yield by heat treatment, and a degradation temperature of the metal organic precursor itself can be decreased. As a result, a high-purity metal film or pattern can be formed at low temperature.

The metal organic precursor disclosed above may further include a neutral ligand (L2). The neutral ligand (L2) may be a ligand binding to the Groups 3 to 12 metal ion (Me), and specifically, may be at least one of (i) an alkene, such as a $C_1$ to $C_{36}$ alkene, (ii) an alkyl, such as a such as a $C_1$ to $C_{36}$ alkyl, (iii) silicon, (iv) an organic ligand having an element selected from sulfur (S), oxygen (O), phosphorus (P), nitrogen (N), or a combination including at least one of the foregoing. Examples of the organic ligand (iv) containing sulfur, oxygen, nitrogen, or a combination including at least one of the foregoing, may include, but are not limited to, an amine compound, an alcohol compound, phosphine, phosphite, a phosphine oxide compound, an arsine compound, a thiol compound, a carbonyl compound, or a combination comprising at least one of the foregoing. Examples of the neutral ligand (L2) may include water ($H_2O$), acetonitrile, isopropyl alcohol, propylamine, or a combination comprising at least one of the foregoing.

In addition, the metal organic precursor disclosed above may be formed in various shapes such as spherical, linear, planar shapes, or a combination including at least one of the foregoing; and may be used in various states such as a particle including a nano particle, powder, or flake, as a colloid, hydride, paste, sol, solution, or a combination including at least one of the foregoing.

The metal organic precursor may further include a solvent or other vehicle. Examples of the solvent or other vehicle may include water; an amine-based solvent; an ester-based solvent; a ketone-based solvent; an aliphatic or aromatic hydrocarbon-based solvent; an ether-based solvent; an alcohol-based solvent; a polyol solvent; an amide solvent; a sulfoxide solvent; an acetate-based solvent; an inorganic solvent; or a combination including at least one of the foregoing. Specifically, the solvent or vehicle may be, but is not limited to, a nitrile-based solvent such as acetonitrile, propionitrile, pentanenitrile, hexanenitrile, heptanenitrile, or isobutylnitrile; an aliphatic hydrocarbon-based solvent such as hexane, heptane, octane, or dodecane; an aromatic hydrocarbon-based solvent such as anisole, mesitylene, or xylene; a ketone-based solvent such as methyl isobutyl ketone, 1-methyl-2-pyrrolidinone, cyclohexanone, or acetone; an ether-based solvent such as tetrahydrofuran, diisobutyl ether, or isopropyl ether; an acetate-based solvent such as ethyl acetate, butyl acetate, or propylene glycol methyl ether acetate; an alcohol-based solvent such as isopropyl alcohol, butyl alcohol, hexyl alcohol, or octyl alcohol; an inorganic solvent; or a combination including at least one of the foregoing.

As further disclosed above, the metal organic precursor disclosed above is a material of which the chelating ligand (L1) and the anion (A) are all easily removed by thermal degradation at a low temperature, and the degradation product of which evaporates at low temperature due to a low melting point or a high vapor pressure. Further, the degradation product generates a material having a reducing property which can reduce the Groups 3 to 12 metal ion to a metal. Thus, when the metallization is performed using the metal organic precursor disclosed above, the reaction may be performed under essentially any atmosphere, and the reaction can be performed at low temperature, and leave no substantial residual impurities.

2. Method of Preparing Metal Organic Precursor

According to another exemplary embodiment, a method of preparing the metal organic precursor disclosed above is provided. Such a method includes the following processes:

preparing a first solution by dissolving a Groups 3 to 12 metal ion (Me)-anion (A) complex in a solvent;

preparing a second solution by dissolving a chelating agent, i.e., a chelating ligand (L1), in a solvent; and mixing the first solution with the second solution.

In an embodiment, the solvent used to prepare the first or second solution may be, but is not limited to, water, acetonitrile, isopropyl alcohol, methanol, or a combination comprising at least one of the foregoing.

The processes may be performed at a low temperature of about 25° C., specifically about 0° C., more specifically about −78° C. or lower to prevent evaporation, for example. For example, the foregoing reactions may be performed in an ice bath to maintain a cooling state.

The Groups 3 to 12 metal ion (Me) may be Cu, Ag, Pt, Pd, Au, Ni, or a combination comprising at least one of the foregoing.

The metal-chelate complex, which comprises the chelating agent, i.e., the chelating ligand (L1), may be a hydrazine alkyl ester represented by Formula II, and the anion (A) may be a compound represented by Formula III.

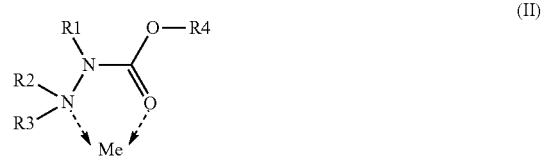

(II)

In Formula II, R1, R2, R3, and R4 are each independently selected from hydrogen, a $C_1$-$C_{10}$ alkyl, $C_6$-$C_{12}$ aryl, $C_1$-$C_{10}$ alkylalkoxy, or $C_6$-$C_{12}$ arylalkoxy, each of which may be unsubstituted or substituted with halogen, amine, —OH, —SH, cyano, sulfonyl, or a combination comprising at least one of the foregoing.

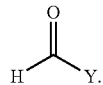

(III)

In Formula (III), Y is oxygen, $C_1$-$C_{10}$ alkyl carboxylate, $C_1$-$C_{10}$ alkyl sulfonate, or a combination comprising at least one of the foregoing.

By preparing the foregoing mixture, a metal organic precursor crystal may be obtained. In addition, the preparation process may include separation, purification, or drying, if desired. For example, a crystal of the metal organic precursor may be washed with ethanol, and then dried at room temperature.

3. Composition Comprising the Metal Organic Precursor

According to still another exemplary embodiment, a conductive ink composition including the metal organic precursor disclosed above is provided. The metal organic precursor composition, for example, may be dissolved in a selected solvent. The solvent may be, but is not limited to, a solvent selected from the following examples i) through xii), or a combination including at least one of the foregoing:

i) water;
ii) an amine-based solvent including a primary amine such as propyl amine, n-butyl amine, hexyl amine, or octyl amine, a secondary amine such as diisopropyl amine, or di(n-butyl) amine, a tertiary amine such as trioctylamine or tri-n-butylamine, an alkyl amine such as ethyl amine, propyl amine, butyl amine, hexyl amine, octyl amine, or trioctyl amine, a cyclic amine, or an aromatic amine;
iii) an ester-based solvent such as poly(ethylene glycol) methylether acrylate ("PEGMEA"), ethyl acetate, n-butyl acetate, r-butyrolactone, 2,2,4-trimethylpentane, diol-1,3-monoisobutyrate, butyl carbitol acetate, butyl oxalate, dibutyl phthalate, dibutyl benzoate, butyl cellosolve acetate, ethylene glycol diacetate, or ethylene glycol diacetate;
iv) a ketone-based solvent such as acetone, methylethylketone, methylisobutylketone, 1-methyl-2-pyrrolidinone, or cyclohexyanone;
v) an aliphatic or aromatic hydrocarbon-based solvent such as toluene, xylene, aromasol, chlorobenzene, hexane, heptane, octane, dodecane, cyclohexane, decane, tetradecane, hexadecane, octadecane, octadecene, nitrobenzene, o-nitrotoluene, anisole, or mesitylene;
vi) an ether-based solvent such as diethylether, dipropylether, dibutylether, dioxane, tetrahydrofuran, diisobutyl ether, isopropyl ether, octyl ether, or tri(ethylene glycol) dimethyl ether;
vii) an alcohol-based solvent such as methanol, ethanol, 1-propanol, 2-propanol, 1-butanol, 2-butanol, isobutanol, hexanol, isopropyl alcohol, ethoxy ethanol, ethyl lactate, ethyleneglycol monomethylether, benzyl alcohol, 4-hydroxy-3-methoxy benzaldehyde, isodeconol, butylcarbitol, terpineol, alpha-terpineol, beta-terpineol, or cineol;
viii) a polyol solvent such as glycerol, glycol, ethylene glycol, diethyl glycol, triethylene glycol, tetraethylene glycol, propylene glycol, dipropylene glycol, butanediol, hexylene glycol, 1,2-pentadiol, 1,2-hexadiol, glycerin, polyethylene glycol, polypropylene glycol, ethyleneglycol monomethylether (methyl cellusolve), ethyleneglycol monoethylether (ethyl cellusolve), ethyleneglycol monobutylether (butyl cellusolve), diethylglycol monoethylether, or diethylglycol monobutylether;
ix) an amide solvent such as N-methyl-2-pyrrolidone ("NMP"), 2-pyrrolidone, N-methylformamide, N,N-dimethyl formamide, or N,N-dimethyl acetamide;
x) a sulfone or sulfoxide solvent such as diethylsulfone, tetramethylene sulfone, dimethyl sulfoxide, or diethylsulfoxide;
xi) an acetate-based solvent such as ethyl acetate, butyl acetate, or propylene glycol methyl ether acetate; or
xii) an inorganic solvent.

In an example, the solvent may be a first solvent such as propylamine, n-butylamine, hexylamine, octylamine, trioctylamine, ethylene glycol, diethylene glycol, triethylene glycol, propylene glycol, dipropylene glycol, hexylene glycol, N-methyl-2-pyrrolidone (ethylene glycol) dimethyl ether, or a combination including at least one of the foregoing; and the second solvent may be ethanol, ethoxy ethanol, methanol, isopropyl alcohol, acetone, tetrahydrofuran, toluene, xylene, ethyl lactate, 2-butanone, octyl ether, water, or a combination including at least one of the foregoing; or the solvent may be a combination of the first solvent and the second solvent.

While not wanting to be bound by theory, it is understood that the first solvent may improve a solubility of the metal organic precursor, and may extend a working life of the composition due to a low vapor pressure, for example. Also, the second solvent can be rapidly removed due to a high vapor pressure, and may reduce a melting point of the metal organic precursor. Thus, when such a mixed solvent is used, a procedure of forming a conductive film or pattern can be more rapidly performed.

While an amount of the metal organic precursor added to the solvent is not particularly limited, when the content of the metal organic precursor is excessively high, it may be difficult to control the size and size distribution of the particles of the metal organic precursor in the composition. In addition, because the viscosity of a suspension is increased during the preparation of the composition, the suspension may be difficult to handle. Contrarily, when the content of the metal organic precursor is excessively low, drying time is increased, and a stacking process may need to be repeated several times to form a film having a desired metal content. For example, the metal organic precursor may be added up to the solubility limit of the metal organic precursor in the solvent. The metal organic precursor may have a solubility of about 20 weight percent (wt %), specifically about 10 wt %, more specifically about 5 wt % in a solvent, based on the total weight of the solution.

If desired, the composition may further include an additive such as a stabilizer, a dispersant, a binder, a reducing agent, a surfactant, a wetting agent, a thixotropic or leveling agent, or a conductor, which is well known in the art.

The stabilizer may be, but is not limited to, an amine compound such as a primary amine, a secondary amine, or a tertiary amine, a bicarbonate-based compound such as an ammonium carbamate, ammonium carbonate, or an ammonium bicarbonate, a phosphorus compound such as a phosphine or a phosphite, a sulfur compound such as a thiol or a sulfide, or a combination including at least one of the foregoing.

The dispersant may be 4000 series dispersant available from EFKA, a DISPERBYK® series dispersant available from BYK, a SOLSPERSE® series available from Avecia, a TEGO® DISPERS series dispersant available from Degussa, a DISPERSE-AYD® series dispersant available from Elementis, or JONCRYL® series available from Johnson Polymer.

The binder may be at least one of an acrylic resin, such as polyacrylate or ester polyacrylate, a cellulose-based resin, such as ethyl cellulose, cellulose ester, or cellulose nitrate, an aliphatic and co-polymeric polyester-based resin, a vinyl-based resin such as polyvinylbutyral, polyvinylacetate, or polyvinylpyrrolidone, a polyamide resin, a polyurethane resin, a polyether and urea resin, an alkyd resin, a silicon resin, a fluorine resin, an olefin-based resin such as polyethylene or polystyrene, a thermoplastic resin or an epoxy resin such as a gasoline or rosin-based resin, an unsaturated or vinyl polyester-based resin, a diallylphthalate-based resin, a phenol-based resin, an oxetane-based resin, an oxazine-based resin, a bismaleimide-based resin, a denatured silicon-based resin such as silicon epoxy or silicon polyester, a thermosetting resin such as a melamine-based resin, an ultraviolet or electron beam curing acrylic resin having a different structure, ethylene-propylene rubber ("EPR"), styrene-butadiene rubber ("SBR"), or a natural polymer such as starch or gelatine.

In addition to the organic resin binder, an inorganic binder such as a glass resin or a glass frit, a silane coupling agent, such as trimethoxy propyl silane or vinyl triethoxy silane, or a titanium-, zirconium- or aluminum-based coupling agent may also be used.

The surfactant may be an anionic surfactant such as sodium lauryl sulfate, a non-ionic surfactant such as nonyl phenoxypolyethoxyethanol, or a ZONYL® FSN material available from Dupont, a cationic surfactant such as laurylbenzylammonium chloride, or an amphoteric surfactant such as lauryl betaine or coco betaine.

The wetting or dispersing agent may be a compound such as polyethyleneglycol, a SURFYNOL® series agent available from Air Products, or a TEGO®wet series agent available from Degussa.

The thixotropic or labeling agent may be BYK series available from BYK, a TEGO Glide® series additive available from Degussa, an EFKA 3000® series additive available from EFKA, or DSX® series additive available from Cognis.

The conductor may be at least one a transition metal such as Ag, Au, Cu, Ni, Co, Pd, Pt, Ti, V, Mn, Fe, Cr, Zr, Nb, Mo, W, Ru, Cd, Ta, Re, Os, and Ir, a main group metals such as Al, Ga, Ge, In, Sn, Sb, Pb, and Bi, lanthanide-based metals such as Sm and Eu, actinide-based metals such as Ac and Th, or any alloy or alloyed oxide thereof, or a combination comprising at least one of the foregoing. The conductor may also be a conductive polymer such as conductive carbon black, graphite, carbon nanotube, polyacetylene, polypyrrole, polyaniline, polythiophene, or a derivative thereof.

The viscosity of the composition is not particularly limited, and may be a viscosity suitable for manufacture of a thin film or a printing method, and may be for example, about 1 milliPascal seconds (mPa·s) to about 1000 Pascal seconds (Pa·s), specifically about 5 mPa·s to about 500 Pa·s, more specifically 10 mPa·s to about 250 Pa·s.

The particle size or amount of the metal organic precursor of the composition to be added may vary depending on the application. For example, the particle size may be 50 micrometers (μm), specifically about 1 nanometer nm to about 25 μm, more specifically about 10 nm to about 1 μm, and may be selected in consideration of the desired thickness of a coated film after heat treatment. The amount of the metal organic precursor to be added is not particularly limited, but the metal organic precursor may be added in an amount that will not make a plasticity temperature too high, or provide problems in application or patterning. In an embodiment, in the total composition, the metal organic precursor may be contained in an amount of about 1 to about 90 weight percent (wt %), specifically about 10 to about 70 wt %, more specifically about 20 to about 60 wt %, based on the total weight of the composition.

4. Method of Forming a Conductive Metal Film or Pattern

A method of forming a conductive metal film or pattern may include: providing the metal organic precursor disclosed above, or a composition including the same; coating the metal organic precursor, or composition including the same, on a substrate; and heat treating.

The metal organic precursor can have excellent reducing characteristics, and be activated at relatively low temperature. For example, a hydrazine-based ligand and an aldehyde-based anion, which are activated by heat treatment, may reduce a Groups 3 to 12 metal ion, and stimulate degradation of the metal organic precursor, thereby providing a pure metal and an organic material, which is removed, by degradation of the metal organic precursor.

In the coating process of the metal organic precursor or composition, the substrate may be formed of, but is not limited to, an inorganic material such as a metal, silicon wafer, glass, quartz, sapphire, SiC, or ceramic, a polymer such as polyimide ("PI"), polyethylene naphthalate ("PEN"), polyethylene terephthalate ('PET"), polyethersulfone ("PES"), polypropylene ("PP"), oriented polypropylene ("oPP"), cycloolefin-based polymer, or polycarbonate ("PC"), a rubber sheet, or a cellulose-based material such as fiber, wood, or paper.

Such a substrate does not need specific treatment, but if desired, may be used after washing and oil-removal, or pretreatment. The pretreatment may be performed using plasma, ion beam, corona, oxidation or reduction, heat, etching, an ultraviolet ray, or by treatment with a primer including a binder or an additive.

In the coating process, the metal organic precursor or the composition including the same may be applied entirely or partially to a surface of the substrate, or if desired, patterned. Alternatively, the metal organic precursor or the composition thereof may be applied to one or both surfaces of the substrate, and the process may be repeated to stack at least two layers of the precursor or composition on the substrate.

To coat the precursor or composition on the substrate, spin coating, roll coating, deep coating, spray coating, dip coating, flow coating, doctor blading, dispensing, inkjet printing, screen printing, gravure printing, offset printing, pad printing, flexography printing, stencil printing, imprinting, xerography, or lithography may be used, but the disclosure is not limited thereto. The coating may be performed using an apparatus such as an inkjet device, a syringe dispensing device, an aerosol jet, an intaglio printer, a roll printer, or a sprayer.

For example, when a pattern is formed by lithography, only a specific part of the metal organic precursor or composition applied to the substrate may be thermally treated and developed using a solvent, thereby obtaining a desired pattern. The partial thermal treatment may be performed by applying UV light to the substrate using a photomask, or by directly irradiating laser or electron-beams an the substrate.

Alternatively, any known patterning methods using heat may be used. For example, soft lithography, imprinting, inkjet printing, silk-screen, or a direct patterning method using electromagnetic waves (such as laser, electron-beams, or UV) are useful.

For example, the term "soft lithography" refers to a method of transferring a pattern formed of an organic compound or material to a substrate using an elastomeric stamp or mold having a desired pattern, as in microcontact printing, microtransfer printing, micro molding in capillary ("MIMIC"), or solvent-assisted micromolding. In soft lithography, a self-assembled monolayer comprising a selected compound is formed on a substrate by contact printing, and a microstructure is formed in a material by embossing (e.g., imprinting) and replica molding.

Forming a pattern using soft lithography may include i) preparing a mold or stamp having a desired pattern, ii) injecting a metal organic precursor or composition on the mold or applying the metal organic precursor or composition to a stamp; and iii) transferring the resulting mold or stamp to a selected substrate and performing heat treatment. The mold or stamp may be comprise polydimethylsilane ("PDMS").

In the heat treatment process, a high-purity metal film may be formed through reduction to provide a metal and degradation of an organic material by heating. A heating temperature may be about 180°, specifically about 160° C. or lower, more specifically about 150° C. or lower, more specifically about 130° C. or lower, more specifically about 120° C. or lower, even more specifically about 100° C. or lower, and the heating may be performed in a substantially inert or in a reducing atmosphere, or in an atmosphere having an oxygen partial pressure, or in air. In other words, regardless of the reaction conditions, the method may provide a metal having high conductivity and high purity, and the metal may also have excellent morphology.

According to the above-described method, without a separate reduction, the Groups 3 to 12 metal ion may be reduced with high efficiency, and may provide a metal film or pattern having high conductivity and high purity by low temperature thermal treatment because a thermal degradation temperature is significantly reduced. In addition, the obtained film or pattern has excellent conductivity and morphology, and includes a ligand chelating the Groups 3 to 12 metal ion, thereby providing excellent stability. The conductive metal film or pattern formed by the above-described method may have a resistivity which is about 10, about 5, about 3, or about 2.5 times that of a corresponding pure bulk metal.

The conductive metal film or pattern may be used for various metal interconnections, or circuits.

In an example, the conductive metal film or pattern may be used for a gate electrode of a semiconductor device, or a gate electrode or source and/or drain electrode of a liquid crystal display device. For example, in a liquid crystal display device including a substrate, a gate electrode formed of the substrate, a semiconductor layer formed on the gate electrode, source and drain electrodes formed on the semiconductor layer and separated from each other, and a pixel electrode electrically connected with the drain electrode, at least one of the gate electrode, the source electrode and the drain electrode may be formed of the conductive metal film or pattern according to the above-described example.

The conductive metal film or pattern may be used as an alternative for a sputter layer of a flexible display or a flat panel display, or the method may be applied to a chemical mechanical planarization ("CMP")-free damascene process and a photoresist ("PR")-free indium tin oxide ("ITO") layer forming process. The conductive metal film or pattern may also be useful in various electronic device fields including a large-sized thin film transistor-liquid crystal display ("TFT-LCD"), a touch screen panel, printed electronics, a solar cell, or in an interconnection.

Hereinafter, the disclosure will be described in further detail with reference to Preparation Examples, Examples, Comparative Examples and Experimental Examples, but the disclosure is not to be limited thereto.

Example 1

A 0.3 mol quantity of copper formate ($Cu(HCOO)_2$), synthesized and dried by adding formic acid to $Cu(OH)_2$, was dissolved in a small quantity of distilled water, thereby preparing a first solution.

A quantity of 2 equivalent weights of hydrazine methyl ester ($NH_2NHCOOCH_3$), which is a ligand, based on the moles of copper, was dissolved in distilled water, thereby preparing a second solution.

The first solution was cooled in an ice bath, and then the second solution was slowly added while being stirred. After the added solution was maintained in the ice bath for 3 hours, blue crystals were separated from the solution, washed with ethanol, and dried.

Example 2

A process was performed using the same method as described in Example 1, except that hydrazine t-butyl ester ($NH_2NHCOO$-tBu) was used as a ligand. Thus, dark blue crystals were produced.

Experimental Example 1

Thermogravimetric analysis ("TGA") of the precursor obtained from Example 1 and the precursor obtained from Example 2 was performed in nitrogen, and thereby a degradation temperature was measured, and a final product was estimated using a weight percent of the final residue. The results are shown in FIGS. 1 and 2.

Referring to FIG. 1, degradation of the precursor of Example 1 started at less than 120° C., a first degradation was performed at 150° C., and the greatest change in weight occurred at 171° C. During the greatest change in weight, an organic ligand and an anion were completely removed. A finally obtained content was almost the same as a theoretical copper content in the precursor, which is 26.3%.

Figure 2:
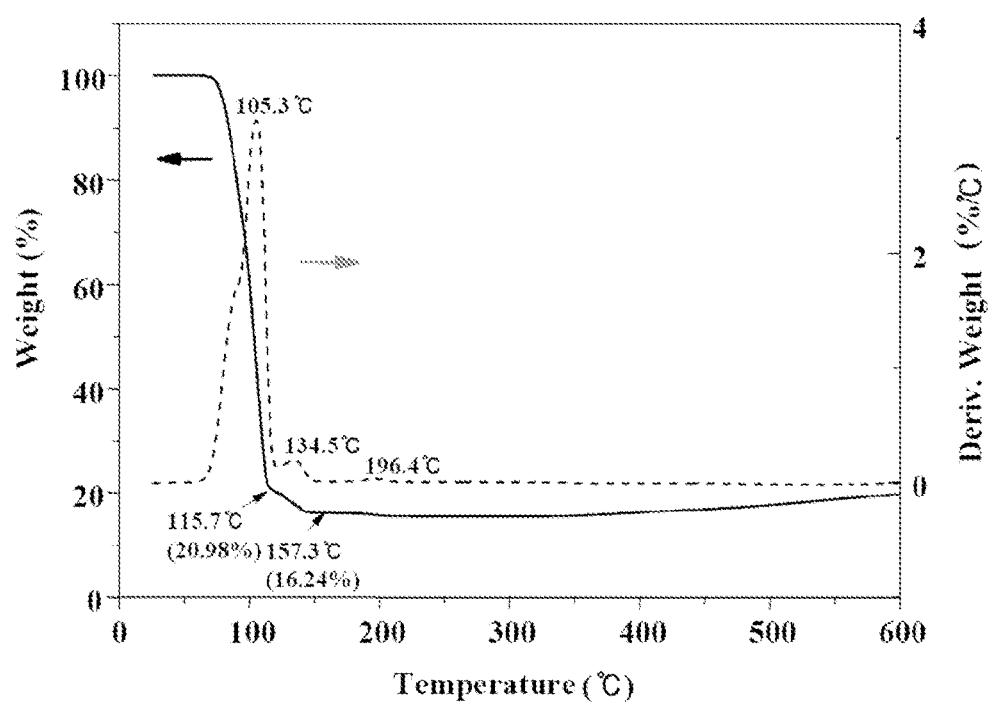
FIG. 2 is a graph of weight (percent, %) and derivative of weight (percent per degrees centigrade, %/° C.) versus temperature (degrees centigrade, ° C.) which shows the TGA result for a metal organic precursor prepared according to Example 2.

Referring to FIG. 2, degradation of the precursor of Example 2 started at less then 70° C. and the greatest change in weight occurred at 171° C. A finally obtained content was almost the same as a theoretical copper content in the precursor, which is 15.6%.

In Examples 1 and 2, the finally remaining compounds had weight percents of 26.23% and 15.57%, respectively, which were almost the same as those of the theoretical copper weights. This means that only pure copper and no oxide remained after the thermal degradation of the compound.

Example 3

A polyimide ("PI") film was closely adhered to a previously-prepared glass plate, and pre-heated on a hot plate maintained at 120° C. The heated glass plate was covered with a bell jar, which is connected with a nitrogen supply apparatus provided to maintain an $N_2$ atmosphere. A drop of a liquid composition, in which the compound of Example 2 was saturated, was applied to the PI film using a long needle, and maintained until a reaction was completed and all solvent was evaporated. The drops of the composition were applied four times, and then the resulting plate was cooled. A sheet resistance of a residue film remaining on the PI film was measured, and the produced material was analyzed using powder XRD. The results are shown in FIG. 3.

Figure 3:
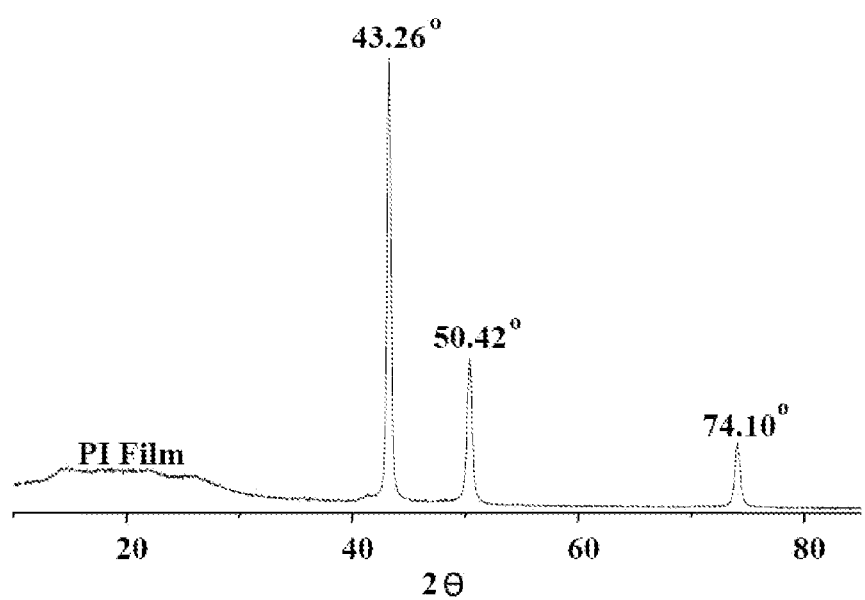
FIG. 3 is a graph of intensity (arbitrary units) versus scattering angle (degrees two-theta, 2θ) which shows the X-Ray Diffraction ("XRD") spectrum for the film prepared according to Example 3.

Referring to FIG. 3, the minimum sheet resistance was measured at 204 microohms per square ($\mu\Omega$/sq), and the XRD analysis shows that the produced material contained pure copper having no copper oxide.

Comparative Example 1

A precursor was synthesized by the same method as described in Example 1, except that, during preparation of a first solution, another anion such as copper nitrate, copper acetate, or copper sulfate replaced copper formate.

When a solution of the synthesized precursor was thermally treated by the same method as Example 3, a black or blue film was formed, and a non-conductive layer, a sheet resistance of which was impossible to measure, was also formed.

While exemplary embodiments have been disclosed herein, it should be understood that other variations may be possible. Such variations are not to be regarded as a departure from the spirit and scope of exemplary embodiments of the present application, and all such modifications as would be obvious to one skilled in the art are intended to be included within the scope of the following claims.

What is claimed is:

1. A metal organic precursor comprising:
   a metal-chelate complex comprising
      a chelate comprising a Groups 3 to 12 metal ion and a chelating ligand, and
      an anion bound to the chelate,
   wherein
      the chelating ligand forms a reducing compound and a volatile material at a temperature of about 160° C. or lower,
      the anion forms a reducing compound and a volatile material at a temperature of 180° C. or lower, and
      the metal-chelate complex is represented by Formula I:

$$[L1\text{-}Me]_p^{n+}[A]_q^{m-} \quad (I)$$

wherein
   Me is the Groups 3 to 12 metal ion,
   L1 is one more of chelating ligands,
   A is an anion compound containing an aldehyde group, or oxalate anion, wherein the anion compound containing an aldehyde group forms OCHO, an alcohol, an alkene, $H_2$, $H_2O$, $CO_2$, or a combination comprising at least one of the foregoing, and is represented by Formula III:

(III)

$$\underset{H}{\overset{O}{\underset{\|}{\text{C}}}}{-}Y$$

wherein Y is oxygen, $C_1$-$C_{10}$ alkyl carboxylate, $C_1$-$C_{10}$ alkyl sulfonate, or a combination comprising at least one of the foregoing,
   n, m, p, and q are independently integers of 1 or more,
   n is a charge quantity of Me, or the sum of a charge quantity of L1 and a charge quantity of Me,
   m is a charge quantity of A, and
   (n×p)=(m×q).

2. The metal organic precursor of claim 1, wherein the Groups 3 to 12 metal ion is Cu, Ag, Pt, Pd, Au, Ni, or a combination comprising at least one of the foregoing.

3. The metal organic precursor of claim 1, wherein the chelating ligand is a hydrazine derivative having an N—N bond and that forms $NH_2$—$NH_2$, an alcohol, an alkene, $H_2$, $H_2O$, $CO_2$, or a combination comprising at least one of the foregoing.

4. The metal organic precursor of claim 3, wherein the chelating ligand is a hydrazine alkyl ester represented by Formula II:

(II)

wherein R1, R2, R3, and R4 are each independently hydrogen, $C_1$-$C_{10}$ alkyl, $C_6$-$C_{12}$ aryl, $C_1$-$C_{10}$ alkylalkoxy, or $C_6$-$C_{12}$ arylalkoxy, each of which may be unsubstituted or substituted with a halogen, amine, —OH, —SH, cyano, or sulfonyl.

5. The metal organic precursor of claim 1, wherein the anion compound containing an aldehyde group is formate.

6. The metal organic precursor of claim 1, wherein the complex represented by Formula I is a metal-chelate complex represented by Formula IV:

(IV)

wherein
   n is an integer of 1 or more;
   Me is a Groups 3 to 12 metal ion;
   X and Y are each independently hydrogen, nitrogen, or oxygen; and
   R1, R2, R3, and R4 when X or Y is nitrogen or oxygen, are each independently selected from hydrogen or a $C_1$-$C_{10}$ alkyl, $C_6$-$C_{12}$ aryl, $C_1$-$C_{10}$ alkylalkoxy, or $C_6$-$C_{12}$ arylalkoxy, each of which may be unsubstituted or substituted with halogen, amine, —OH, —SH, cyano, sulfonyl, or a combination comprising at least one of the foregoing.

7. The metal organic precursor of claim 1, wherein L1 comprises a neutral ligand.

8. The metal organic precursor of claim 7, wherein the neutral ligand is an alkene, an alkyl, silicon, or an organic ligand having an element selected from sulfur, oxygen, phosphorus, nitrogen (N), or a combination comprising at least one of the foregoing.

9. The metal organic precursor of claim 1, further comprising water; an amine-based solvent; an ester-based solvent; a ketone-based solvent; an aliphatic or aromatic hydrocarbon-based solvent; an ester-based solvent; an alcohol-based solvent; a polyol solvent; an amide-based solvent; a sulfoxide-based solvent; an acetate-based solvent; an inorganic solvent; or a combination comprising at least one of the foregoing.

10. The metal organic precursor of claim 1, wherein a metallization temperature of the metal organic precursor is about 150° C. or lower.

11. A method of forming a conductive metal film, the method comprising:
preparing a metal organic precursor, the metal organic precursor comprising a metal-chelate complex comprising
a chelate comprising a Groups 3 to 12 metal ion and a chelating ligand, and
an anion bound to the chelate,
wherein
the chelating ligand forms a reducing compound and a volatile material at a temperature about 160° C. or lower,
the anion forms a reducing compound and a volatile material at a temperature of about 180° C. or lower, and
the metal-chelate complex is represented by Formula I:

$$[L1\text{-}Me]_p^{n+}[A]_q^{m-} \qquad (I),$$

wherein
Me is the Groups 3 to 12 metal ion,
L1 is one more of chelating ligands,
A is an anion compound containing an aldehyde group, or oxalate anion, wherein the anion compound containing an aldehyde group forms OCHO, an alcohol, an alkene, $H_2$, $H_2O$, $CO_2$, or a combination comprising at least one of the foregoing, and is represented by Formula III:

(III)

wherein Y is oxygen, $C_1$-$C_{10}$ alkyl carboxylate, $C_1$-$C_{10}$ alkyl sulfonate, or a combination comprising at least one of the foregoing,
n, m, p, and q are independently integers of 1 or more,
n is the sum of a charge quantity of L1 and a charge quantity of Me,
m is a charge quantity of A, and
(n×p)=(m×q);
coating the metal organic precursor on a substrate; and
heat treating the metal organic precursor to form a conductive metal film.

12. The method of claim 11, wherein the substrate includes a semiconductor; an inorganic material; a polymer; a cellulose-based material; or a combination comprising at least one of the foregoing.

13. The method of claim 11, wherein the substrate includes a semiconductor; a metal, a silicon wafer, a glass, a ceramic, a polyimide, a polyethylene naphthalate, a polyethylene terephthalate, a polyestersulfone, a polypropylene, an oriented polypropylene, a cyclo-olefin polymer, a polycarbonate, a rubber sheet, a fabric, wood, paper, or a combination comprising at least one of the foregoing.

14. The method of claim 11, wherein the coating the metal organic precursor is performed by spin coating, roll coating, deep coating, spray coating, dip coating, flow coating, doctor blading, dispensing, inkjet printing, screen printing, gravure printing, offset printing, pad printing, flexography printing, stencil printing, imprinting, xerography, or lithography.

15. The method of claim 11, wherein the heat treating is performed at 180° C. or lower.

16. A composition comprising the metal organic precursor of claim 1.

* * * * *